United States Patent [19]
Matsuno

[11] Patent Number: 5,782,751
[45] Date of Patent: Jul. 21, 1998

[54] SIDE VIEW ENDOSCOPE

[75] Inventor: Shinichi Matsuno, Tokyo, Japan

[73] Assignee: Asahi Kogaku Kogyo Kabushiki Kaisha, Tokyo, Japan

[21] Appl. No.: 449,847

[22] Filed: May 24, 1995

[30] Foreign Application Priority Data

May 26, 1994 [JP] Japan ................... 6-112398
May 26, 1994 [JP] Japan ................... 6-112399

[51] Int. Cl.$^6$ ............................................ A61B 1/012
[52] U.S. Cl. ....................... 600/157; 600/127; 600/170
[58] Field of Search ............................ 600/121, 125, 600/127, 158, 157, 170

[56] References Cited

U.S. PATENT DOCUMENTS

| | | | |
|---|---|---|---|
| 3,903,877 | 9/1975 | Terada | 600/157 |
| 4,311,134 | 1/1982 | Mitsui et al. | 600/157 X |
| 4,436,087 | 3/1984 | Ouchi | |
| 4,747,661 | 5/1988 | Ohkuwa | 600/170 X |
| 4,841,949 | 6/1989 | Shimizu et al. | 600/158 X |
| 4,860,731 | 8/1989 | Matsuura | 600/157 |
| 4,960,106 | 10/1990 | Kubokawa et al. | 600/127 X |
| 5,325,847 | 7/1994 | Matsuno | 600/170 X |
| 5,329,935 | 7/1994 | Takahashi | 600/121 |
| 5,386,817 | 2/1995 | Jones | 600/157 X |
| 5,518,501 | 5/1996 | Oneda et al. | 600/127 |

FOREIGN PATENT DOCUMENTS 6014865   1/1994   Japan ................... 600/127

OTHER PUBLICATIONS

Japanese Utility Model No. Sho–64–6804, Published Feb. 22, 1989.

Primary Examiner—John P. Leubecker
Attorney, Agent, or Firm—Kane, Dalsimer, Sullivan, Kurucz, Levy, Eisele and Richard, LLP

[57] ABSTRACT

A side view type endoscope includes a front end body having a view window on the side surface thereof, a detachable front end cover which covers the front end body, an opening provided on the side surface of the front end cover, through which the view window is exposed to the exterior, air and/or water supply passages which supply cleaning air and/or water, and a nozzle connected to the air and/or water supply passages to selectively inject air or water toward the view window, wherein the air and/or water supply passages are provided on said front end body and the nozzle is provided on the front end cover.

4 Claims, 9 Drawing Sheets

5,782,751

1

SIDE VIEW ENDOSCOPE

BACKGROUND OF THE INVENTION

1. Field of the Invention

The present invention relates to an endoscope, and more precisely to a side view type endoscope having a view window provided on a side surface of a front end body thereof.

2. Description of Related Art

There is a known side view type endoscope which is provided, on a side surface of a front end body thereof, with a view window and an illumination window provided adjacent to the view window. The outer surface of the portion of the front end body other than the view window and the illumination window is entirely covered by a front end cover. The front end body is provided with a nozzle secured thereto, whose front injection port opens toward the outer surface of the view window. The nozzle selectively injects air or water onto the surface of the view window through the injection port to clean the view window.

In the known side view type endoscope as mentioned above, since the nozzle is permanently secured to the front end body, it is difficult or troublesome to clean the nozzle and air and water supply passages connected to the nozzle.

An answer to this problem is to provide a nozzle which can be detachably attached to the front end body. Heretofore, various front view type endoscopes provided with detachable nozzles have been proposed. However, it is difficult to provide such a nozzle to a conventional side view type endoscope, since the nozzle is disposed on the side surface of the front end body.

SUMMARY OF THE INVENTION

The primary object of the present invention is to provide a side view type endoscope in which the interior of the nozzle and the air and water supply passages connected to the nozzle can be easily cleaned.

To achieve the object mentioned above, according to the present invention, there is provided a side view type endoscope including a front end body having a view window on the side surface thereof, a detachable front end cover which covers the front end body, an opening provided on the side surface of the front end cover, through which the view window is exposed to the exterior, air and/or water supply passages which supply cleaning air and/or water, and a nozzle connected to the air and/or water supply passages to selectively inject air or water toward the view window, wherein the air and/or water supply passages are provided on the front end body and the nozzle is provided on said front end cover.

Preferably, the side view type endoscope further comprises an engaging projection provided on the end cover, and an engaging recess provided on the end body, in which the engaging projection is fitted to prevent the front end cover from being accidentally disengaged from the front end body.

The engaging projection can be provided with a connecting hole which constitutes a part of the nozzle, to which the air supply passage and the water supply passage are connected when the engaging projection is fitted in the engaging recess.

The front end cover and said front end body can be provided with a second engaging projection and a second engaging recess in which the second engaging projection is fitted to prevent the front end cover from being accidentally detached from the front end body.

2

In an embodiment, the first and second engaging projections are made of a resilient material of which the front end cover is made.

The front end cover can be comprised of an elastically deformable body member, and a deformation restricting member whose elasticity is lesser than that of the body member, and wherein at least the second engaging projection is supported by the deformation restricting member.

Preferably, the air supply passage and said water supply passage are formed adjacent and parallel within the front end body, the connecting hole provided in the engaging projection comprises a connecting groove which extends in a direction perpendicular to the longitudinal direction of the front end body, so that the air supply passage and the water supply passage open in to the connecting groove.

The connecting hole can be provided with a discharge hole which is connected at one end thereof to the connecting groove and which opens at the other end toward the view window.

According to another aspect of the invention, there is provided a side view type endoscope includes a front end body having a recess which forms an end surface perpendicular to an axis of the front end body, air and/or water supply passages which supply cleaning air and/or water, an open end of the air and/or water supply passages being opened at the end surface of the front end body, a detachable front end cover which covers the front end body, a nozzle provided on the front end cover, the nozzle being connected to the open end of the air and/or water supply passages.

The present disclosure relates to subject matter contained in Japanese patent application Nos. 6-112398 (filed on May 26, 1994) and 6-112399 (filed on May 26, 1994) which are expressly incorporated herein by reference in their entireties.

BRIEF DESCRIPTION OF THE DRAWINGS

The invention will be described below in detail with reference to the accompanying drawings, in which.

DESCRIPTION OF THE PREFERRED EMBODIMENT

An improved side view type endoscope according to a first embodiment of the present invention, free from the above-mentioned drawbacks will be discussed below with reference to FIGS. 1 through 5.

Figure 1:
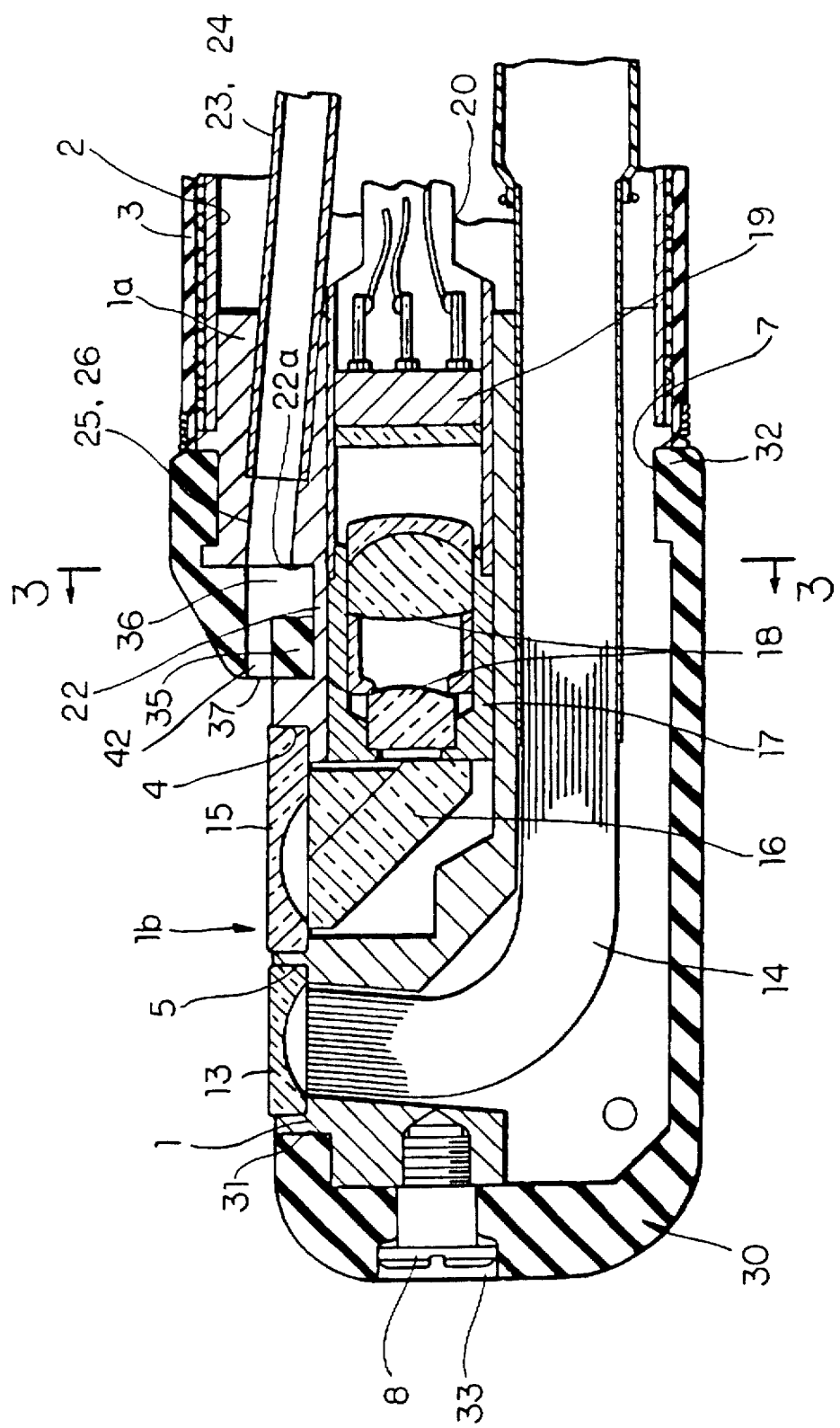
FIG. 1 is a side sectional view of a front end portion of a side view type endoscope according to the present invention.
Figure 2:
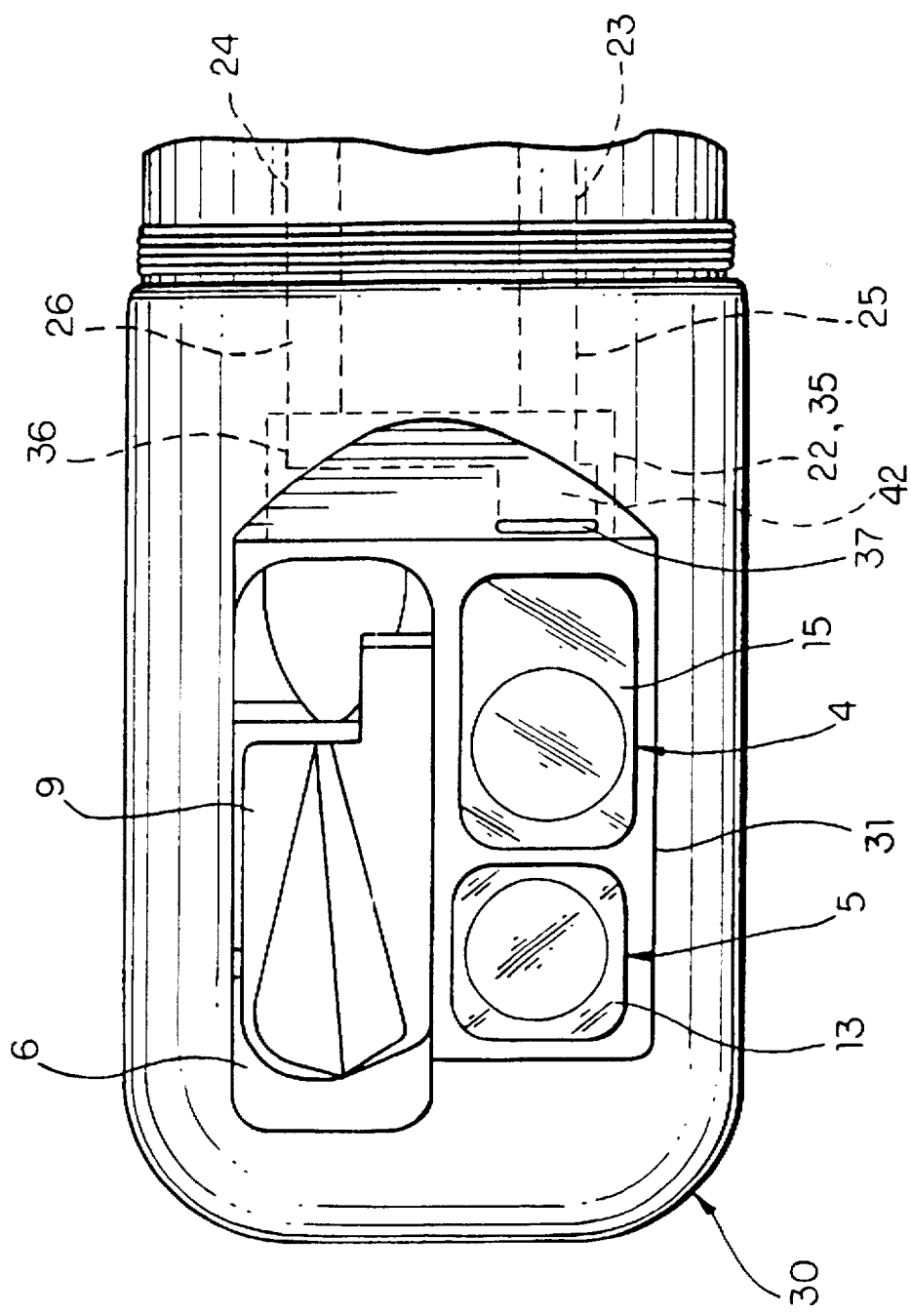
FIG. 2 is a plan view of a front end portion of a side view type endoscope shown in FIG. 1.
Figure 3:
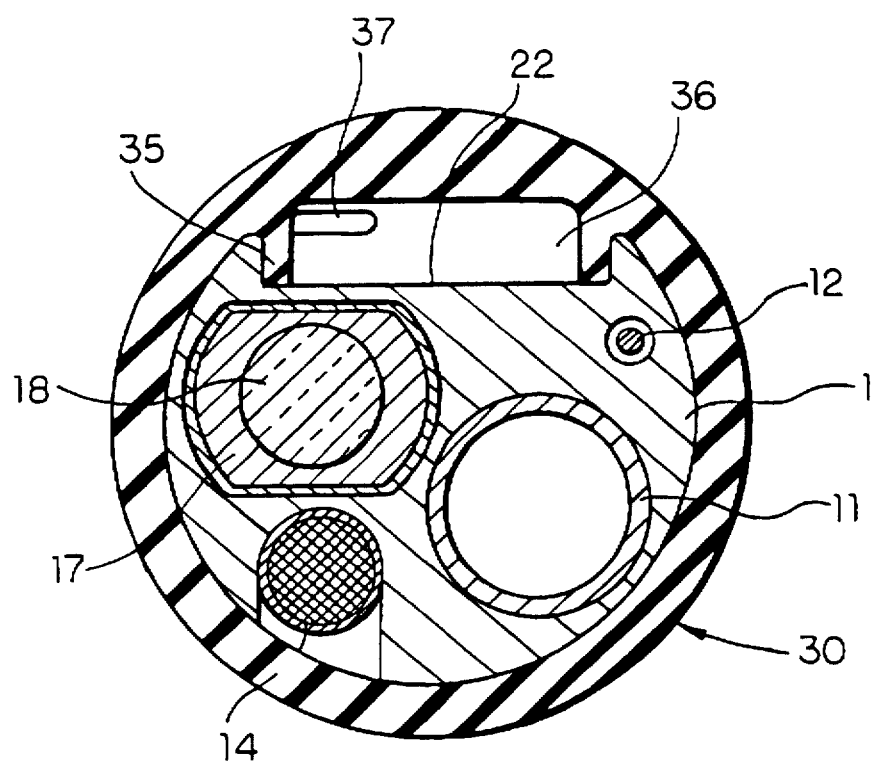
FIG. 3 is a sectional view of a front end portion of a side view type endoscope, taken along the line III—III in FIG. 1.
Figure 4:
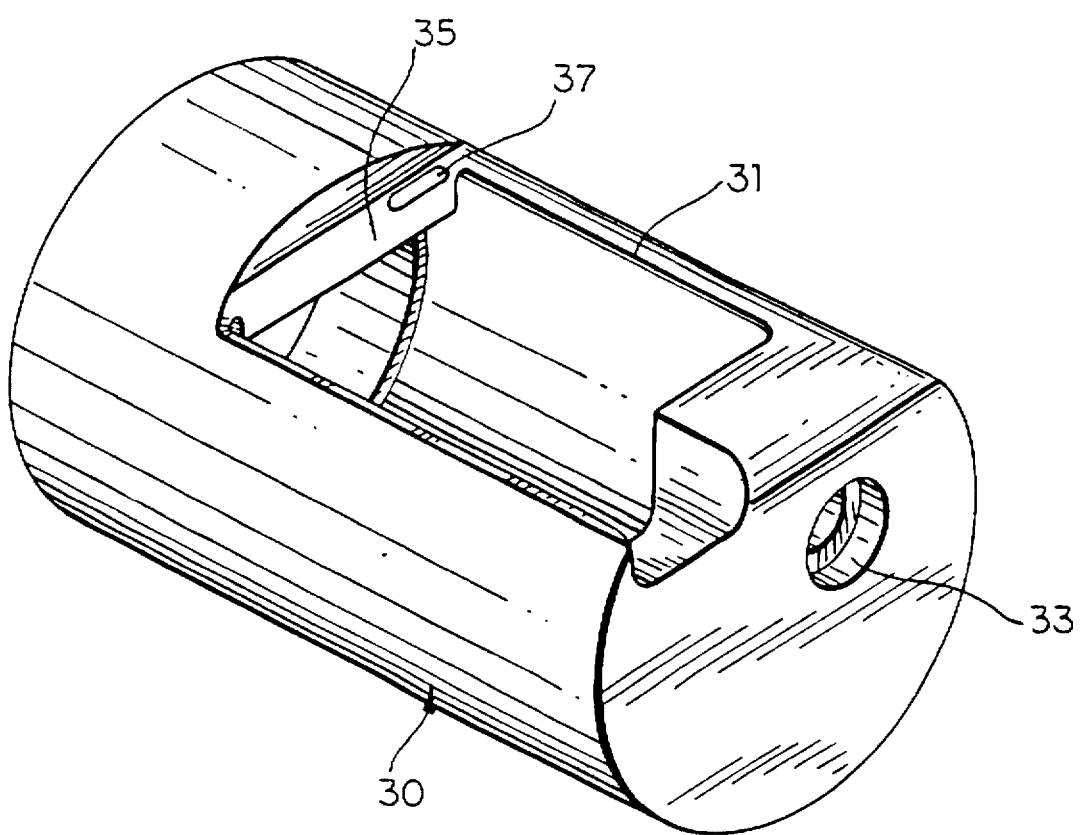
FIG. 4 is a perspective view of a front end cover which covers a front end portion of a side view type endoscope shown in FIG. 1.

The front end body 1 of the side view type endoscope is made of a generally circular metal rod having a partially flat surface portion 1b, as shown in FIGS. 1 and 3. The front end body 1 is provided on the flat surface portion 1b thereof with a view window 4, an illumination window 5, and a treatment tool insertion opening 6 (FIG. 2). The flat surface portion is defined by the remaining circular rod portion (extruding portion) 1a which is located behind (right side of the flat surface portion 1b in FIG. 1) the flat surface portion 1b. The front end body 1 including the extruding portion 1a is fitted in a front opening 2 of a flexible endoscope for attaching the front end body 1 to the endoscope. A flexible rubber tube 3 seals the outer periphery of the front opening 2 of the endoscope, as shown in FIG. 1.

As can be seen in FIG. 1, the illumination window 5 is provided with an orientation lens 13 made of a concave lens fitted and secured therein for diffusing the illumination light incident thereto. A bundle of optical fibers (optical fiber bundle) 14 is provided below the orientation lens 13 for transmitting illumination light to the orientation lens 13. The emission end of the fiber bundle 14 is opposed to the orientation lens 13.

The view window 4 is provided with a cover lens 15 for a viewing optical system secured thereto. The front end body 1 includes a prism 16 located below the cover lens 15 to deflect the optical axis of the viewing optical system by 90 degrees, an objective lens 18 and a solid state image pickup device 19. The objective lens 18 and the solid state image pickup device 19 are provided in a lens barrel 17. The solid state image pickup device 19 is comprised of, for example, a charge coupled device (CCD) and has a light receiving surface located at an image forming position in which an object image is formed by the objective lens 18. The CCD 19 is connected to an operating portion (not shown) through a signal cable 20 which extends rearward within the endoscope.

The front end body 1 is provided with a recessed groove 22 having a flat bottom surface, located behind the cover lens 15, as shown in FIGS. 1, 2 and 3. The recessed groove 22 has a lateral width substantially identical to the width of the flat surface portion 1b of the front end body 1 and a predetermined length in the longitudinal direction of the endoscope.

The recessed groove 22 is defined by a vertical rear end wall 22a which is provided with an air supply passage 25 and a water supply passage 26. The air supply passage 25 and the water supply passage 26, both of which open into the recessed groove 22 are connected to an air supply pipe 23 and a water supply pipe 24, respectively.

The portion of the front end body 1 other than the view window 4, the illumination window 5, and the treatment tool insertion opening 6 is entirely covered by a front end cover 30 which is made of a water-tight resilient material, such as resilient fluororubber. The front end cover 30 is in the form of a cap having a closed front end and an open rear end. The front end cover 30 is provided with an opening 31 corresponding to the view window 4, the illumination window 5, and the treatment tool insertion opening 6.

The front end cover (end cap) 30 is attached to the front end of the front end body 1, while expanding the diameter of the front end cover 30. The front end cover 30 is provided on the rear end thereof with a first engaging projection in the form of an inner peripheral flange 32 which slightly projects inwardly. The inner peripheral flange 32 is fitted in a peripheral first engaging recess or groove 7 formed on the extruding portion 1a of the front end body 1 when the front end cover 30 is attached to the front end of the front end body 1, so as to prevent the accidental detachment of the front end cover 30 from the front end body 1. The end cap 30 is provided on the front end thereof with a hole 33 having a spot facing in which a machine screw 8 is inserted to be screwed in a corresponding threaded hole of the front end body 1 to firmly attach the end cap 30 to the front end body 1.

The end cap 30 is also provided with a projection 35 providing a second engaging projection corresponding to the recessed groove 22 of the front end body 1 which provides a second engaging recess, so that when the end cap 30 is attached to the front end body 1, the projection 35 is airtightly fitted in the recessed groove 22. The projection 35 has a flat bottom surface (inner surface) that faces inwardly. Consequently, when the engaging projection 35 is fitted in the engaging recessed groove 22, the flat bottom surface of the projection 35 comes into contact with the bottom surface of the recessed groove 22, thereby, preventing the relative rotation of the end cap 30 and the front end body 1 from taking place.

The front end cover 30 is provided with an elongated connecting groove 36 formed in the latter half of the projection 35 and extending in a direction perpendicular to the longitudinal axis of the endoscope. The air supply passage 25 and water supply passage 26 are formed adjacent and parallel and open into a discharge passage 42 of the connecting groove 36 when the front end cover 30 is attached to the front end body 1.

A nozzle 37 which is directly connected to the connecting groove 36 opens into the front wall of the projection 35 of the front end cover 30. The nozzle 37 is located in the vicinity of the cover lens 15 so that when the front end cover 30 is attached to the front end body 1, the front end of the nozzle 37 faces the outer surface of the cover lens 15. Consequently, air or water fed through the air supply pipe 23 or the water supply pipe 24 is injected from the nozzle 37 through the connecting groove 36 onto the outer surface of the cover lens 15.

A remote-control type treatment tool 9 is provided within the treatment tool inserting opening 6 to which a front end of a treatment tool insertion channel 11 (FIG. 3) formed in the front end body 1 is connected. As shown in FIG. 3, an operation wire 12 is provided within the front end cover 30 so as to swing the treatment tool 9 by a remote control (not shown) during treatment.

In using the endoscope as constructed above, the cleaned front end cover (end cap) 30 is attached to the cleaned front end body 1. Upon attachment, the inner peripheral flange 32 and the projection 35, etc., are elastically deformed (expanded) due to the elasticity of the front end cover 30. When the front end cover 30 is securely attached to the front end body 1, the inner peripheral flange 32 and the projection 35, etc., are returned to their initial state due to the elastic restoring force, so that the inner peripheral flange 32 and the projection 35 are firmly engaged in the peripheral groove 7 and the recessed groove 22, respectively. Thereafter, the machine screw 8 is inserted in the hole 33 of the front end cover 30 and screwed in the threaded hole of the front end body 1 to steadfastly secure the front end cover 30 to the front end body 1.

In this state, the view window 4, the illumination window 5, and the treatment tool insertion opening 6 are exposed to the outside through the opening 31; the nozzle 37 faces the outer surface of the cover lens 15; and, the air supply passage 25 and the water supply passage 26 are connected to the connecting groove 36.

Figure 5:
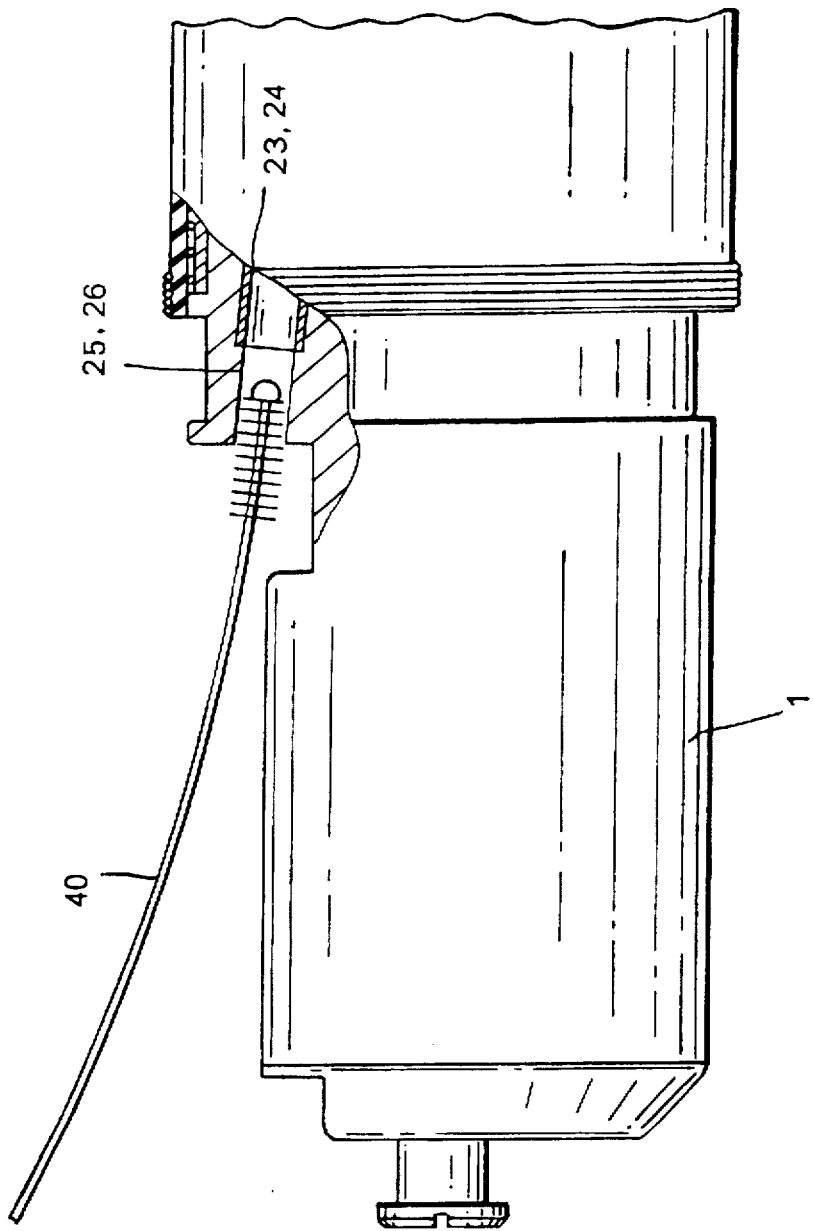
FIG. 5 is a partially sectioned side view of a side view type endoscope with a removed front end cover.

To wash or clean the endoscope after use, the machine screw 8 is loosened and disengaged from the hole 33 the front end cover 30 is slid rearward with respect to the front end body 1 while expanding the rear end thereof. Consequently, the front end cover 30 is detached from the front end body 1. Thereafter, a cleaning brush 40 is inserted into the air supply passage 25 or the water supply passage 26, that is exposed by removing the front end cover 30 to brush and clean the air supply pipe 23 or the water supply pipe 24, as can be seen in FIG. 5. Furthermore, the nozzle 37 which is formed in the removed front end cover 30 can be easily cleaned from the front end side or rear end side thereof.

As can be understood from the above discussion, according to the present invention, the nozzle 37 which is adapted to inject a cleaning fluid toward the outer surface of the view window 4 is formed in the front end cover 30 which is detachably attached to the front end body 1 of the endoscope, the nozzle formed in the front end cover 30 and the fluid supply passages (air/water supply passages 25/26 and air water supply pipes 23/24) formed in the front end body 1 can be easily and completely cleaned or washed when the front end cover 30 is removed from the front end body 1 after the endoscope is used.

Moreover, since the relative position of the front end cover 30 to the view window 4 of the front end body 1 is automatically determined when the front end cover 30 is attached to the front end body 1, no adjustment of the orientation of the nozzle 37, during assembling, is necessary, thus resulting in a simple assembling operation.

FIGS. 6 through 9 show a second embodiment of an endoscope according to the present invention.

In the second embodiment, the front end cover 30 is formed of two different materials, unlike the first embodiment. The other structure of the endoscope in the second embodiment is substantially identical to that of the endoscope according to the first embodiment, and accordingly, the elements corresponding to those in the first embodiment are designated with like reference numerals, and no detailed explanation thereof will be given herein.

Figure 6:
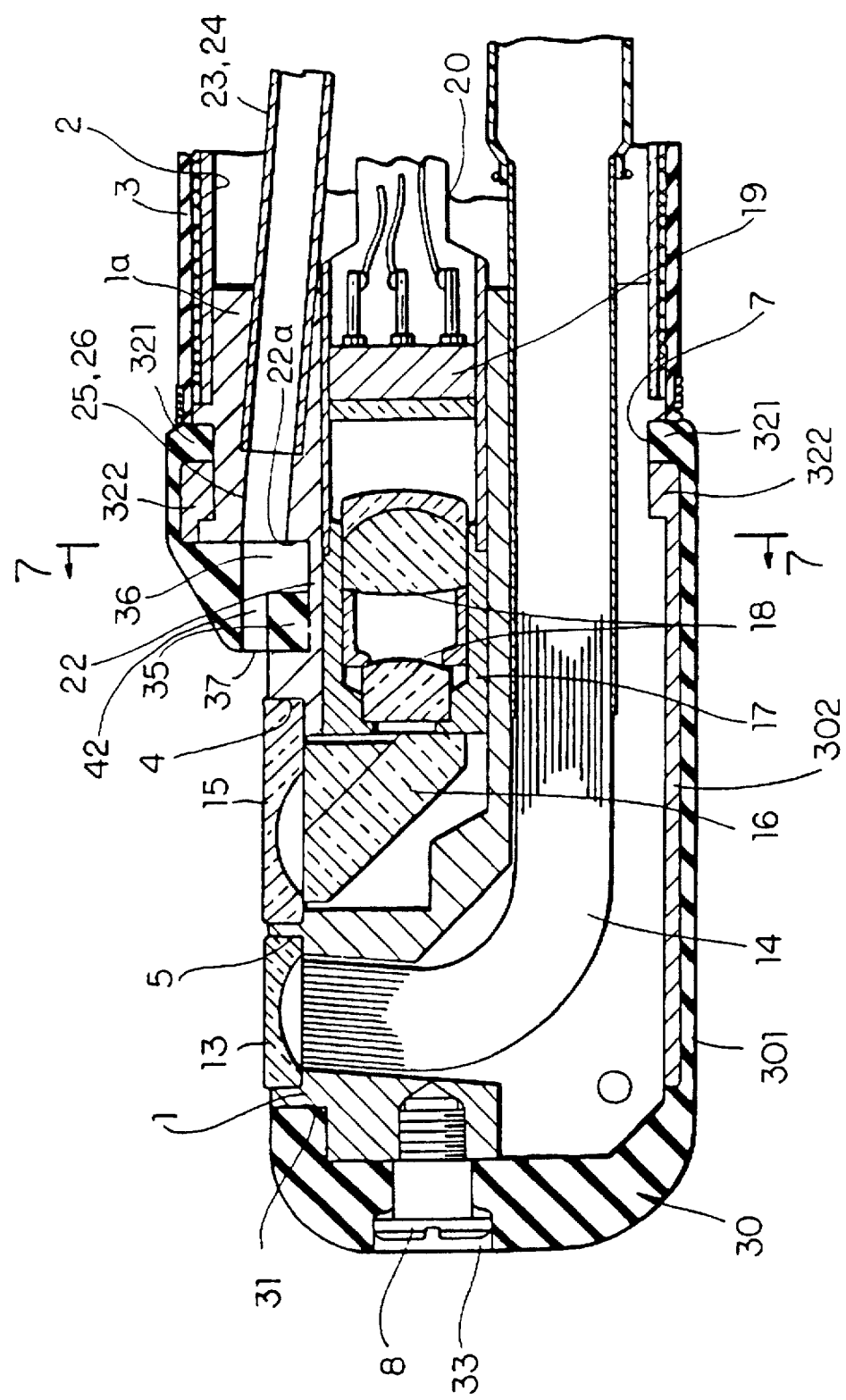
FIG. 6 is a side sectional view of a front end portion of a side view type endoscope, according to another embodiment of the present invention.
Figure 7:
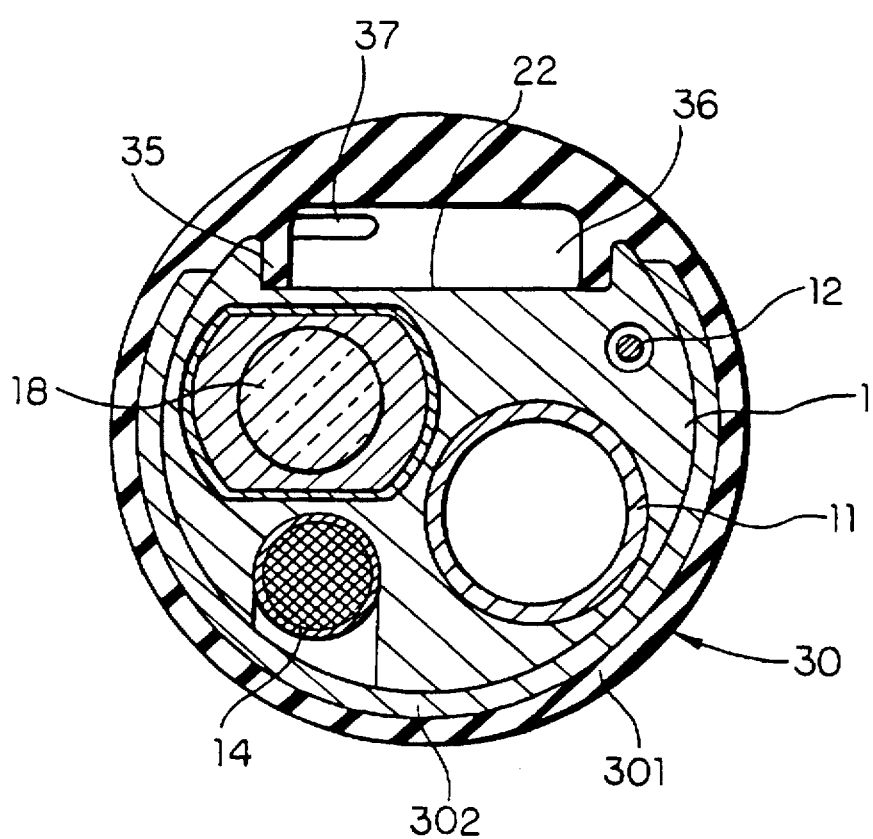
FIG. 7 is a sectional view of a front end portion of a side view type endoscope, taken along the line VIII—VIII in FIG. 6.
Figure 8:
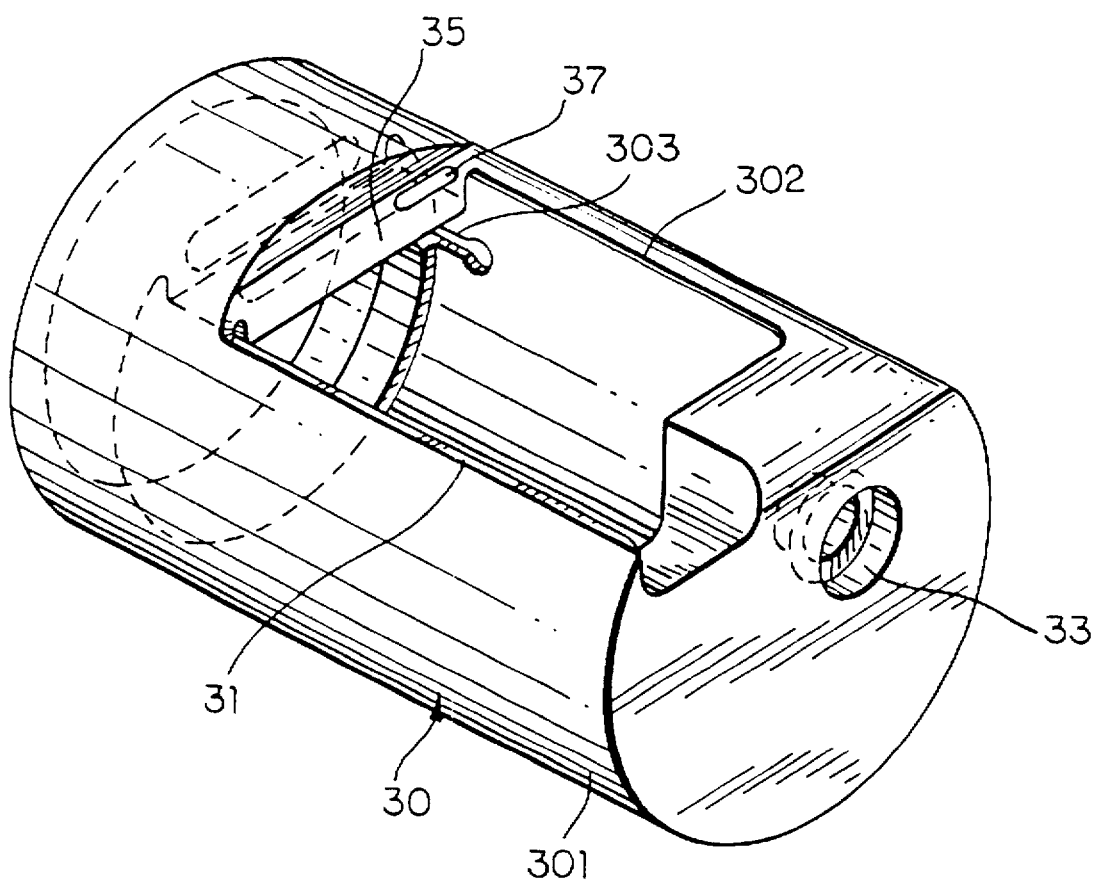
FIG. 8 is a perspective view of a front end cover which covers a front end portion of a side view type endoscope shown in FIG. 6; and, FIG. 9 is a perspective view of a front end cover shown in FIG. 6, with a cover frame indicated by a phantom line.
Figure 9:
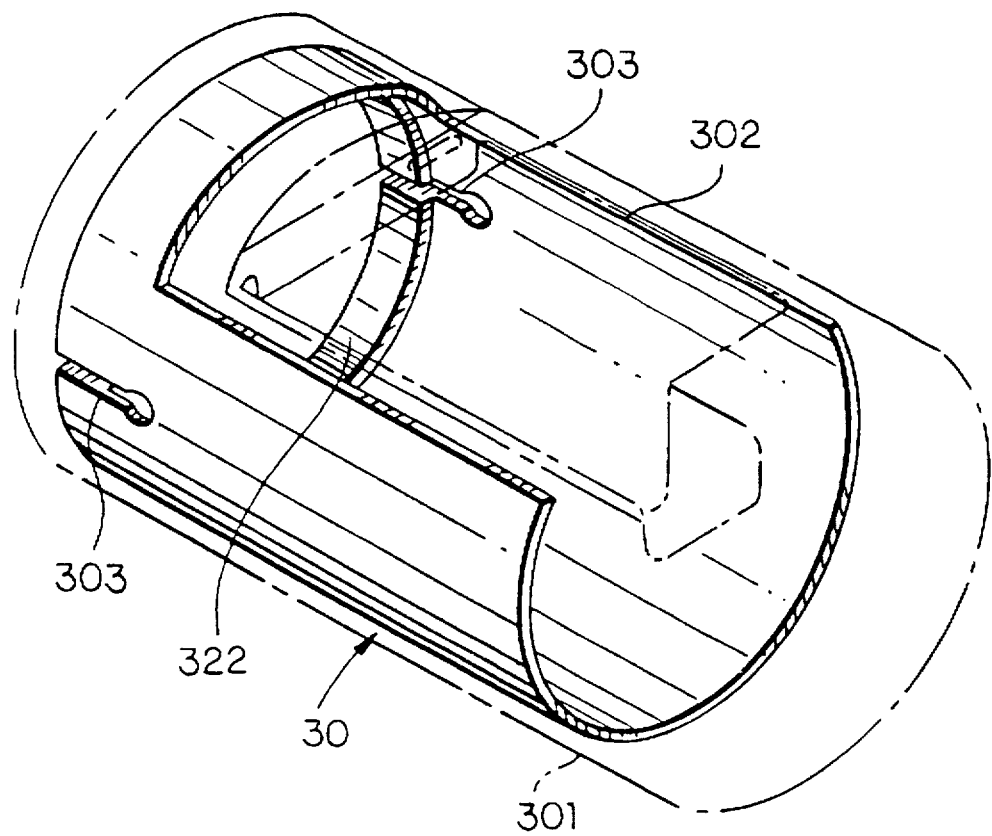

In FIG. 6, the end cap (front end cover) 30 is comprised of a main body 301 formed of a resilient elastically deformable material such as fluororubber, and a partial cover frame 302 provided on a part of the inner surface of the main body 301 to restrict the deformation of the main body 301. The cover frame 302 is provided only on the portion of the inner surface of the main body 301 that would otherwise contact the inner surface of the front end body 1. As shown in FIG. 9, the cover frame 302 is in the form of a ring at the rear end thereof (left side in FIG. 9), and the remaining portion of the cover frame 302 is generally "C"-shaped to define an upper opening corresponding to the view window 4.

The material of the cover frame 302 is not formed of a material having high resiliency like rubber, but instead the cover frame 302 is formed of a metal or plastic to exhibit a slight elastic deformability. The main body 301 is aligned with the cover frame 302 integrally adhered thereto.

The main body 301 and the cover frame 302 of the front end cover 30 are provided on the rear ends thereof with inner peripheral flanges 321 and 322 that are fitted in the peripheral groove 7 formed on the front end body 1 so as to prevent the front end cover 30 from being accidentally disengaged from the front end body 1 when the front end cover 30 is attached to the front end body 1.

The inner peripheral flange 321 and the inner peripheral flange 322 are formed of the same material as that of the main body 301 and the cover frame 302, respectively. Therefore, the inner peripheral flange 321 has the same resiliency as the main body 301 and the inner peripheral flange 322 has the same elasticity as the cover frame 302. The resilient inner peripheral flange 321 is supported by the hard inner peripheral flange 322. The cover frame 302 is provided on the annular rear end thereof with a pair of diametrically opposed slits 303 which open at the rear ends. The slits 303 facilitate the attachment of the front end cover 30 to the front end body 1.

The nozzle 37 connected to the connecting groove 36 opens into the front end wall of the projection 35 of the main body 301 of the front end cover 30, similar to the first embodiment.

When the endoscope as constructed above is used, the cleaned front end cover (end cap) 30 is attached to the cleaned front end body 1. Upon attachment, the inner peripheral flanges 321 and 322 and the projection 35, etc., are elastically deformed (expanded) due to the elasticity of the front end cover 30. When the front end cover 30 is secured to the front end body 1, the inner peripheral flanges 321, 322 and the projection 35, etc., are returned to their initial state due to the elastic restoring force, so that the inner peripheral flanges 321, 322 and the projection 35 are firmly engaged in the peripheral groove 7 and the recessed groove 22, respectively.

It should be noted that upon deformation, the cover frame 302 prevents the main body 301 from being excessively deformed. Specifically, an adequate deformation of the front end cover 30 takes place when the latter is attached to the front end body 1, thereby, ensuring that the front end cover 30 is securely attached to the front end body 1. When the front end cover 30 is attached to the front end body 1, the inner peripheral flanges 321 and 322 of the front end cover 30 are engaged in the peripheral groove 7 of the front end body 1. Thus, the front end cover 30 can be firmly secured to the front end body 1 without being accidentally detached therefrom.

Thereafter, the machine screw 8 is inserted in the hole 33 of the front end cover 30 and screwed in the threaded hole of the front end body 1 to steadfastly secure the front end cover 30 to the front end body 1.

In this state, the view window 4, the illumination window 5, and the treatment tool insertion opening 6 are exposed to the outside through the opening 31; the nozzle 37 faces the outer surface of the cover lens 15; and, the air supply passage 25 and the water supply passage 26 are connected to the connecting groove 36.

Since the air and water supply passages between the connecting groove 36 and the outlet port of the nozzle 37 are air-tight and water-tight sealed by the resilient main body 301 with respect to the front end body 1, there is no leakage of air or water therethrough.

As can be understood from the above discussion, according to the present invention, since the front end cover 30 is provided with the main body 301 formed of a resilient material and the cover frame 302 defining a deformation restricting member which restricts the elastic deformation of the main body 301, no excess deformation of the main body occurs upon attachment of the front end cover 30 to the front end body 1 of the endoscope. Consequently, an adequate elastic deformation of the main body necessary to attach the front end cover 30 to the front end body 1 takes place, so that the front end cover 30 can be securely attached to the front end body 1.

Moreover, according to the present invention, since the nozzle 37 which is adapted to inject a cleaning fluid toward the outer surface of the view window 4 is formed in the front end cover 30 which is detachably attached to the front end body 1 of the endoscope, the nozzle 37 formed in the front end cover 30 and the fluid supply passages (air/water supply passages 25/26 and air/water supply pipes 23/24) formed in the front end body 1 can be easily and completely cleaned or washed when the front end cover 30 is removed from the front end body 1 after the endoscope is used.

Although the invention has been described with reference to particular means, materials and embodiments, it is understood that the invention is not limited to the illustrated embodiments but extends to all equivalents within the scope of the following claims.

I claim:

1. A side view endoscope comprising:

a front end body having a view window on a side surface thereof;

a detachable front end cover which covers said front end body;

an opening provided on a side surface of said front end cover exposing said view window;

an air supply passage and a water supply passage formed within said front end body, said air supply passage for supplying air and said water supply passage for supplying water;

a nozzle formed and contained directly within said detachable front end cover, said nozzle comprising an enclosed passageway having an open end directly communicating outside said front end cover and not through said front end body;

means for connecting said nozzle to said at least one of said air and water supply passages when said detachable front end cover is attached to said front end body so that air and water can be ejected from said nozzle toward said view window;

a first engaging projection provided on said detachable front end cover;

a first engaging recess provided on said end body, said first engaging projection being fitted in said first engaging recess and aligned with said nozzle to eliminate fluctuation of said front end cover when air or water is ejected from said nozzle;

a second engaging projection provided on said detachable front end cover; and a second engaging recess provided on said front end body, said second engaging projection being fitted in said second engaging recess to prevent said detachable front end cover from being accidentally detached from said front end body;

wherein said first engaging projection is provided with a connecting groove which constitutes a part of said nozzle, said at least one of said air supply passage and said water supply passage being connected to said connecting groove when the first engaging projection is fitted in the first engaging recess: and, wherein said air supply passage is adjacent and parallel to said water supply passage and said connecting groove extends perpendicularly to a longitudinal axis of the front end body so that the air supply passage and the water supply passage open into the connecting groove.

2. A side view endoscope according to claim 1, wherein said first and second engaging projections are formed of a resilient material of which the front end cover is formed.

3. A side view type endoscope according to claim 1, further comprising a discharge passage which is connected at one end thereof to the connecting groove and which opens at the other end toward the view window.

4. A side view endoscope comprising:

a front end body having a view window on a side surface thereof;

a detachable front end cover which covers said front end body;

an opening provided on a side surface of said front end cover exposing said view window;

at least one of an air supply passage and a water supply passage provided in said front end body, said air supply passage for supplying air and said water supply passage for supplying water;

a nozzle formed and contained directly within said detachable front end cover, said nozzle comprising an enclosed passageway having an open end directly communicating outside said front end cover and not through said front end body;

means for connecting said nozzle to said at least one of said air and water supply passages when said detachable front end cover is attached to said front end body so that air and water can be ejected from said nozzle toward said view window;

a first engaging projection provided on said detachable front end cover;

a first engaging recess provided on said end body, said first engaging projection being fitted in said first engaging recess and aligned with said nozzle to eliminate fluctuation of said front end cover when air or water is ejected from said nozzle;

a second engaging projection provided on said detachable front end cover; and a second engaging recess provided on said front end body, said second engaging projection being fitted in said second engaging recess to prevent said detachable front end cover from being accidentally detached from said front end body wherein said front end cover comprises an elastically deformable body and a deformation restriction member, said deformation restricting member having an elasticity lesser than the elastically deformable body and wherein at least the second engaging projection is supported by the deformation restricting member.

* * * * *